(12) United States Patent
Hess et al.

(10) Patent No.: US 8,034,034 B2
(45) Date of Patent: Oct. 11, 2011

(54) SYRINGE AND METHOD OF USE

(75) Inventors: Brian J. Hess, Charlestown, MA (US);
Richard L. Walker, Jr., West Bridgewater, MA (US); Liem T. Vu, Needham, MA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 12/319,815

(22) Filed: Jan. 12, 2009

(65) Prior Publication Data
US 2010/0179507 A1 Jul. 15, 2010

(51) Int. Cl.
*A61M 5/315* (2006.01)

(52) U.S. Cl. ............ 604/226; 604/57; 604/64; 604/187; 604/218; 604/236; 606/94

(58) Field of Classification Search .................. 604/500, 604/506, 57–60, 64, 181, 183, 187, 218, 604/220, 226, 236; 606/92–94
See application file for complete search history.

(56) References Cited

U.S. PATENT DOCUMENTS

| | | | |
|---|---|---|---|
| 2,647,512 A | 8/1953 | Johnson | |
| 4,490,142 A | 12/1984 | Silvern | |
| 4,625,722 A * | 12/1986 | Murray | 606/95 |
| 4,784,607 A | 11/1988 | Francois | |
| 4,915,701 A | 4/1990 | Halkyard | |
| 4,958,622 A | 9/1990 | Selenke | |
| 4,995,867 A | 2/1991 | Zollinger | |
| 5,697,903 A | 12/1997 | Fischer | |
| 6,283,946 B1 | 9/2001 | Fischer | |
| 6,309,372 B1 | 10/2001 | Fischer et al. | |
| 6,582,438 B2 | 6/2003 | DeMayo | |
| 6,620,169 B1 | 9/2003 | Peterson et al. | |
| 7,041,085 B2 | 5/2006 | Perez et al. | |
| 7,306,390 B2 * | 12/2007 | Quintero et al. | 401/133 |
| 2006/0247652 A1 | 11/2006 | Heinz | |
| 2007/0185495 A1 | 8/2007 | Hess et al. | |
| 2007/0225654 A1 | 9/2007 | Hess et al. | |
| 2008/0125722 A1 | 5/2008 | Hess et al. | |
| 2008/0228192 A1 | 9/2008 | Beyar et al. | |
| 2008/0300575 A1 * | 12/2008 | Cleator et al. | 604/514 |

OTHER PUBLICATIONS

International Search Report and Written Opinion, PCT/US10/20611, dated Mar. 2, 2010, 7 pages.

* cited by examiner

*Primary Examiner* — Bhisma Mehta
(74) *Attorney, Agent, or Firm* — Lerner, David, Littenberg, Krumholz & Mentlik, LLP

(57) ABSTRACT

A syringe and a method of using the syringe are disclosed. The syringe includes a longitudinal body having proximal and distal ends and including an aperture between the proximal and distal ends. An injectable material, such as an adhesive bone cement, may be loaded into the body of the syringe through the aperture. After the injectable material is inserted, the aperture may be closed by covering the aperture with an aperture cover. The aperture cover may be configured to slide into a position covering the aperture, or the aperture cover may be placed in a position covering the aperture, such as by pivoting about a hinge. After the aperture is closed, the injectable material may be dispensed from the distal end of the syringe body by depressing a plunger. Depressing the plunger may initiate the closing of the aperture, or the aperture may be closed independently of plunger movement.

36 Claims, 12 Drawing Sheets

SYRINGE AND METHOD OF USE

BACKGROUND OF THE INVENTION

Bone cement is commonly used by surgeons in order to fill voids in bone. It would be desirable to use bone cement, such as an adhesive bone cement, to hold small bone fragments in place to allow for healing, when methods such as traditional plate and screw methods of reattachment are not feasible. Only a small amount of bone cement may be required to fill small gaps between the bone fragments in order to glue the fragments together. For example, volumes of cement under one cubic centimeter may be used. In such applications, the cement material may be delivered to the repair site through a delivery system, such as a syringe having a cannulated needle.

The bone cement may be a mixture of different ingredients, and, before applying the bone cement to a repair site, the cement may be prepared by mixing it in a bowl with a pestle. Prepared bone cements can have various viscosities, and some may have quite a high viscosity, with a consistency like a tacky paste. For example, a typical adhesive bone cement may have a viscosity greater than 80 pascal-seconds. The prepared bone cement can be transferred to the syringe through the opening in the proximal end of the syringe, which is made accessible by removing the plunger from the syringe.

The prepared cement material can be difficult to pour into the proximal end of an application syringe, especially when it has a high viscosity. Additionally, the opening at the proximal end of the syringe may be quite small, thus making the pouring of the bone cement into the syringe even more difficult. The pouring of the bone cement into the proximal end of the syringe can also be time consuming, which can be problematic when the curing time for the cement is relatively short. Furthermore, the material which is poured into the proximal end of the syringe can develop air pockets along the syringe barrel. Air pockets can detrimentally cause pressure spikes during injection of the cement. These pressure increases can cause filter pressing, where the liquid portion of the cement separates from the powder portion. This can result in the liquid being squeezed out of the syringe, leaving behind a dense mass of powder, which can jam the syringe.

BRIEF SUMMARY OF THE INVENTION

One aspect of the present invention provides a syringe. The syringe according to this aspect of the invention desirably includes an elongated body having a longitudinal axis and defining an open interior portion adapted to contain an injectable material. The body preferably has a proximal end and a distal end, the distal end being adapted to dispense the injectable material therefrom. The body preferably includes an aperture which provides access to the open interior portion of the body, the aperture preferably being located between the proximal and distal ends. The syringe according to this aspect of the invention desirably includes a plunger at least partially disposed within the open interior portion of the body. The plunger is preferably configured to slide along the longitudinal axis for dispensing the injectable material through the distal end of the body. The syringe according to this aspect of the invention desirably includes a closure coupled to the plunger, the closure being operable to close the aperture in the body. Preferably, according to this aspect of the invention, the plunger is operable to operate the closure to close the aperture in the body.

In accordance with this aspect of the invention, the closure may include a cover slidably coupled to the plunger. The cover is preferably configured to slide between an open position and a closed position, wherein the cover covers the aperture in the closed position.

Another aspect of the present invention provides a syringe for dispensing an injectable material. The syringe according to this aspect of the invention desirably includes an elongated body having an open interior adapted to contain an injectable material. The body preferably has a lateral aperture which provides access to the open interior of the body. The syringe according to this aspect of the invention desirably includes a plunger slidably received at least partially within the open interior of the body. The plunger is preferably moveable between at least a first and second position within the body. The syringe according to this aspect of the invention desirably includes a cover coupled to the plunger, the cover closing the aperture when the plunger is in the second position. In accordance with this aspect of the invention, the plunger may be moveable to a third position beyond the first and second positions, wherein the injectable material has been dispensed from the body when the plunger is in the third position.

In accordance with any or all aspects of the invention, the cover may be configured to slide along a linear path aligned with the longitudinal axis of the body. In other aspects, the cover may be configured to slide along an arcuate or a helical path aligned around the longitudinal axis of the body.

Yet another aspect of the present invention provides a syringe. The syringe according to this aspect of the invention desirably includes an elongated body having a longitudinal axis and defining an open interior portion adapted to contain an injectable material. The body preferably has a proximal end and a distal end, the distal end being adapted to dispense the injectable material therefrom. The body preferably includes an aperture which provides access to the open interior portion of the body, the aperture preferably being located between the proximal and distal ends. The syringe according to this aspect of the invention desirably includes a dispensing means which is movable within the open interior portion of the body for dispensing the injectable material from the distal end of the body. The syringe preferably also includes a closing means which is responsive to movement of the dispensing means for closing the aperture in the body.

Another aspect of the present invention provides a method for dispensing an injectable material from a syringe. A method according to this aspect of the invention desirably includes the step of providing a syringe having a proximal end and a distal end and including an aperture therein between the proximal and distal ends. The aperture preferably provides access to an open interior portion of the syringe. The syringe preferably further includes a plunger which is moveable within the open interior portion of the syringe. The method desirably also includes the step of inserting an injectable material into the open interior portion of the syringe through the aperture. The method preferably also includes the step of depressing the plunger to sequentially close the aperture and dispense the injectable material from the distal end of the syringe.

Further, in accordance with this aspect of the invention, the step of inserting the injectable material into the open interior portion of the syringe may comprise inserting a loading device having the injectable material thereon through the aperture, and transferring the injectable material into the open interior portion.

In accordance with any or all aspects of the invention, the injectable material may be bone cement.

DETAILED DESCRIPTION

Figure 1:
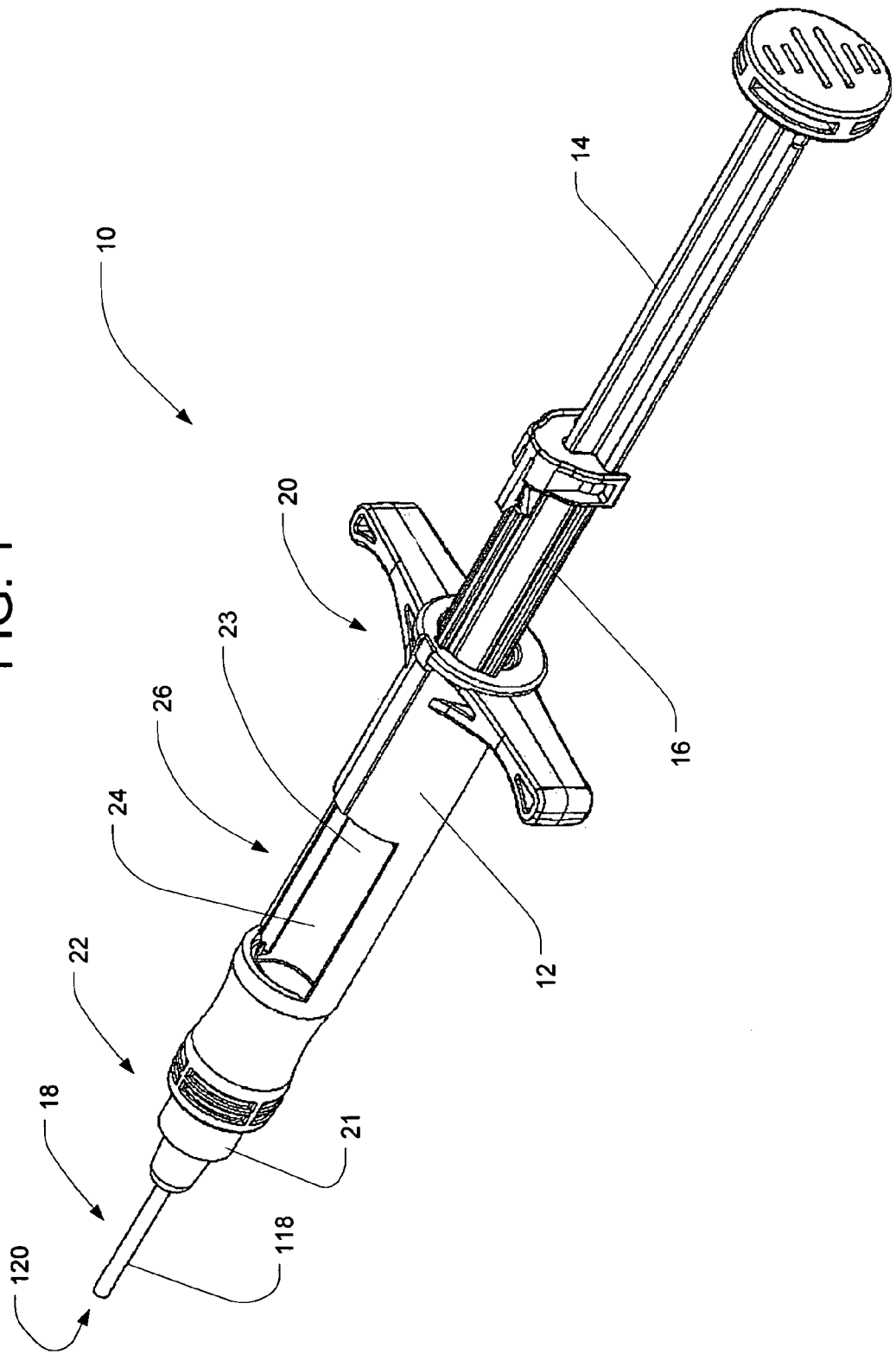
FIG. 1 is a perspective view of a syringe in accordance with one embodiment of the invention in a first operating state.

In describing the preferred embodiments of the invention illustrated in the appended drawings, in which like reference numerals represent like elements, specific terminology will be used for the sake of clarity. However, the invention is not intended to be limited to the specific terms so selected, and it is to be understood that each specific term includes all technical equivalents that operate in a similar manner to accomplish a similar purpose.

A syringe 10 in accordance with one embodiment of the present invention is illustrated in FIG. 1. The syringe 10 includes a longitudinal body 12, a dispensing means (such as a plunger 14), a closure or closing means (such as an aperture cover 16), and a dispensing structure (such as a dispensing tip 18). The syringe body 12 has a proximal end 20 and a distal end 22. The dispensing tip 18 is attached to the body 12 at the distal end 22 by a coupling portion, such as a luer connection 21.

Figure 2:
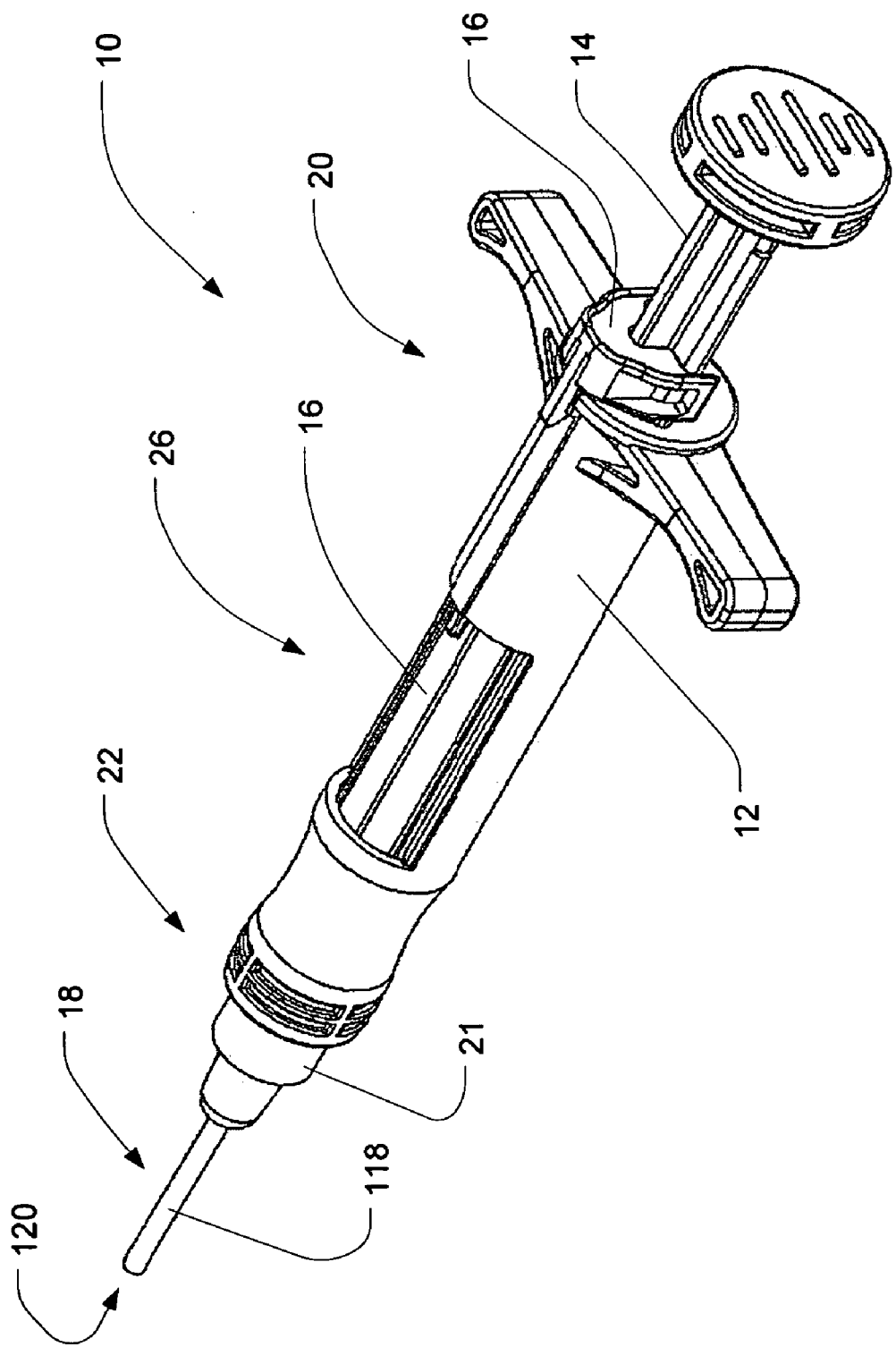
FIG. 2 is a perspective view of the syringe of FIG. 1 showing the syringe in a second operating state.

The syringe body 12 is hollow and includes a passage 23 therealong forming an open interior portion 24. The body includes an aperture 26 which provides access to the open interior portion 24. The aperture 26 is configured so that bone cement may be inserted into the interior portion 24 through the aperture 26. After inserting the bone cement into the syringe 10, the aperture may be closed by sliding the aperture cover 16 distally until it covers the aperture 26, as shown in FIG. 2. Once the aperture 26 is closed, the bone cement may be dispensed from the dispensing tip 18 by sliding the plunger 14 distally along the passage 23, which collects the bone cement in the distal end 22 of the body 12 and pushes the cement through the dispensing tip 18. In other embodiments of the invention, the dispensing tip need not be included, and the cement may be dispensed directly from an opening in the distal end of the body. The components of the syringe 10 and the method for using the syringe 10 are described in more detail below.

Figure 3:
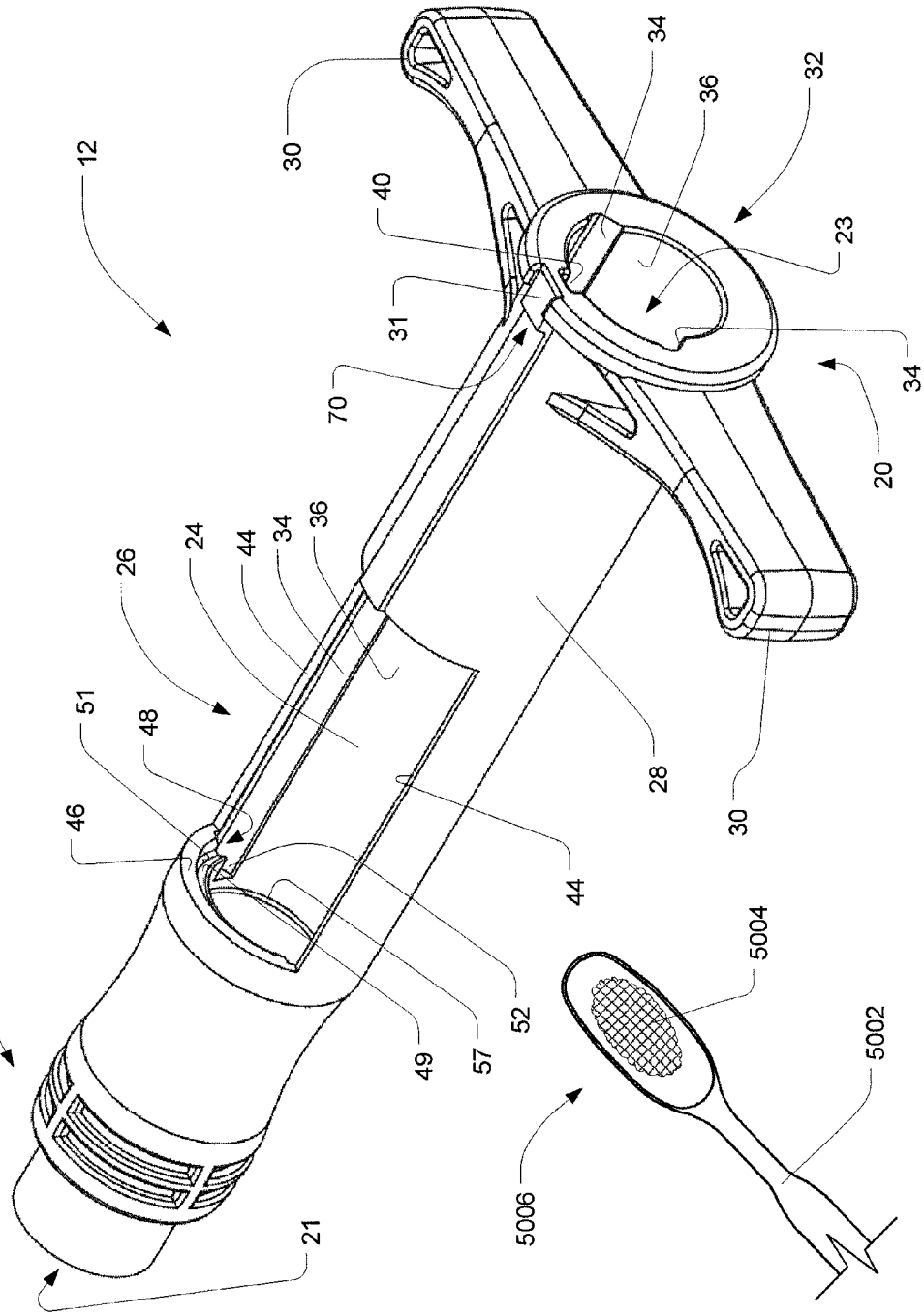
FIG. 3 is a perspective view of a syringe body in accordance with one embodiment of the invention.

The syringe body 12 is illustrated in FIG. 3. The body 12 is substantially cylindrical, and the passage 23 forming the open interior portion 24 is defined by a sidewall 28. The proximal end 20 of the syringe body 12 has two finger grips 30 in the form of extensions projecting from the sidewall 28 of the body 12. The finger grips 30 are preferably large enough and sturdy enough that the user can get enough leverage during injection. Since the cement material stiffens during the time it is being prepared and dispensed, a large injection force (for example, up to 150 Newtons) may be required. The proximal end 20 of the syringe body 12 also preferably includes a projection 31 which is configured to engage a locking member 33 at the proximal end 35 of the aperture cover 16. The proximal end 20 of the body 12 also includes an opening 32 at the proximal end of the passage 23 that forms the open interior portion 24. The passage 23 is configured to receive the plunger 14 and allow the plunger 14 to slide along the open interior portion 24.

The body 12 of the syringe 10 includes a guiding structure for guiding the aperture cover 16 along the body 12 in the longitudinal direction. The guiding structure may include grooves 34 formed in the cylindrical inner surface 36 of the body 12. For example, as illustrated in FIG. 3, the grooves 34 may be located opposite one another across the diameter of the cylindrical inner surface 36. The grooves 34 are configured to receive guiding rails 38 of the aperture cover 16, in order to support the cover 16 and guide the cover 16 to slide in the longitudinal direction of the body 12, therefore preventing rotation of the cover 16 around the longitudinal axis of the body 12. The body 12 may include additional guiding structures, such as groove 40, which is configured to receive projection 42 on the aperture cover 16, in order to provide additional guidance for the aperture cover 16. The inner surface 36 of the body 12 is preferably recessed between the grooves 34 in order to accommodate the aperture cover 16.

The aperture 26 in the sidewall 28 of the body 12 is preferably located approximately halfway down the length of the body 12. The length of the body 12 may be, for example, approximately three inches long, and the length of the aperture 26 may be approximately one inch long. Preferably the aperture 26 is slightly longer than the loading device that is used to insert the bone cement into the open interior portion 24 of the body 12. The aperture 26 has side edges 44 substantially aligned with the longitudinal axis of the body 12. An angle defined between the side edges 44 of the aperture 26 and taken about the longitudinal axial centerline of the body is preferably no greater than 180°, so that the cement material is unlikely to fall out of the aperture 26 when it is inserted into the open interior portion 24 and it is unlikely to squeeze out of the aperture 26 when the aperture cover 16 is closed. The above-described angle of the aperture 26 is preferably between 90° and 180° inclusive. More preferably the angle is approximately 150°.

Figure 8:
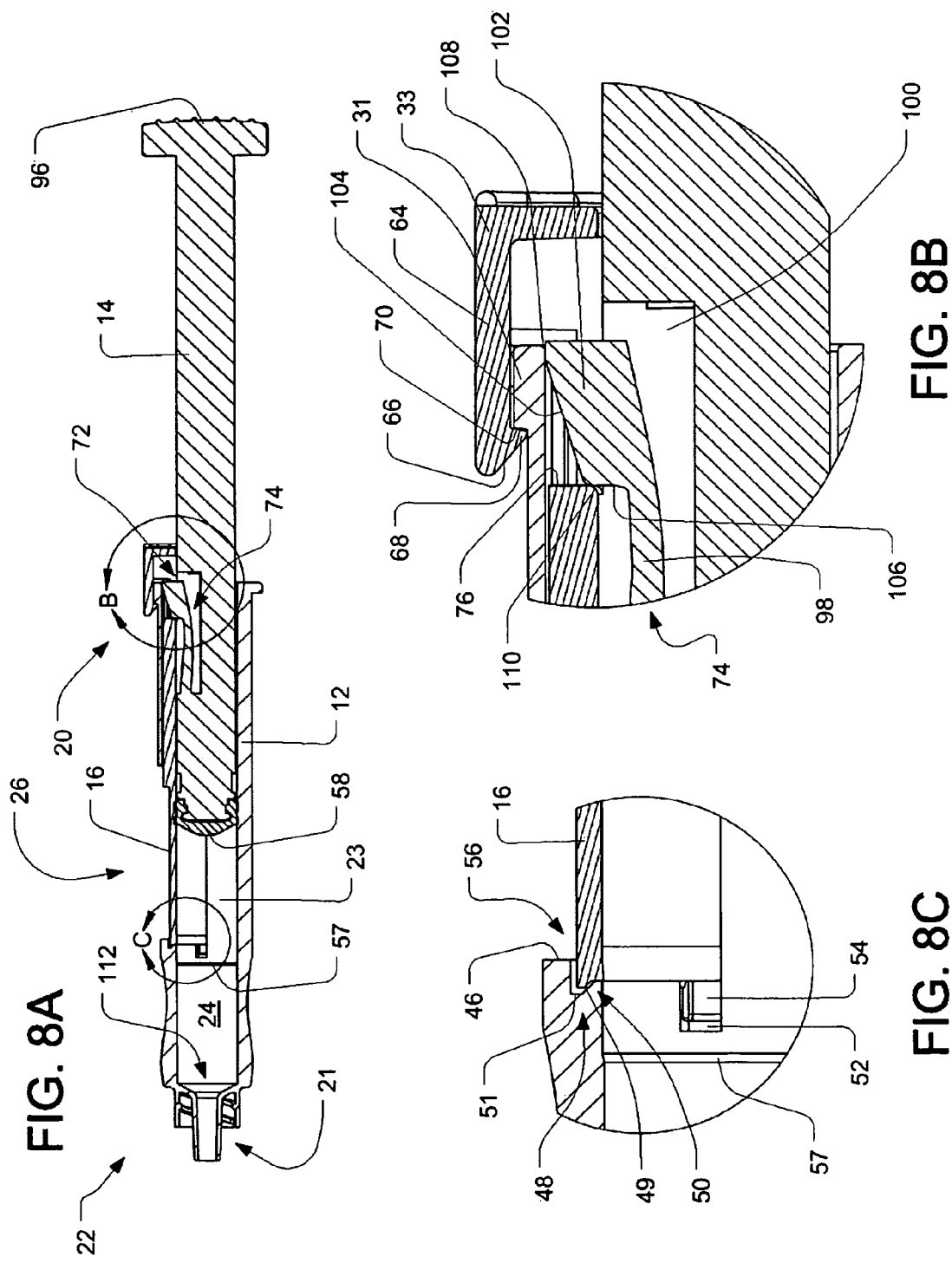
FIG. 8A is a sectional view of the syringe of FIG. 6 shown in a third operating state.
FIG. 8B is an enlarged sectional view of section B in FIG. 8A.
FIG. 8C is an enlarged sectional view of section C in FIG. 8A.

The distal edge 46 of the aperture 26 includes a groove 48 therein configured to receive the distal edge 50 of the aperture cover 16, in order to provide a more secure connection between the aperture cover 16 and the body 12. Preferably this connection substantially prevents cement from squeezing out of the aperture 26 when the aperture cover 16 is closed. As shown in FIG. 3 and FIG. 8C, the groove 48 may include an angled surface 49 adjoining a surface 51 perpendicular to the longitudinal axis of the body 12. The distal edge 50 of the aperture cover 16 preferably has a matching profile. Preferably such a configuration of the groove 48 assists in providing a secure connection between the aperture cover 16 and the body 12, as the angled surface 49 preferably guides the distal edge 50 of the aperture cover 16 into proper engagement with the groove 48.

Figure 4:
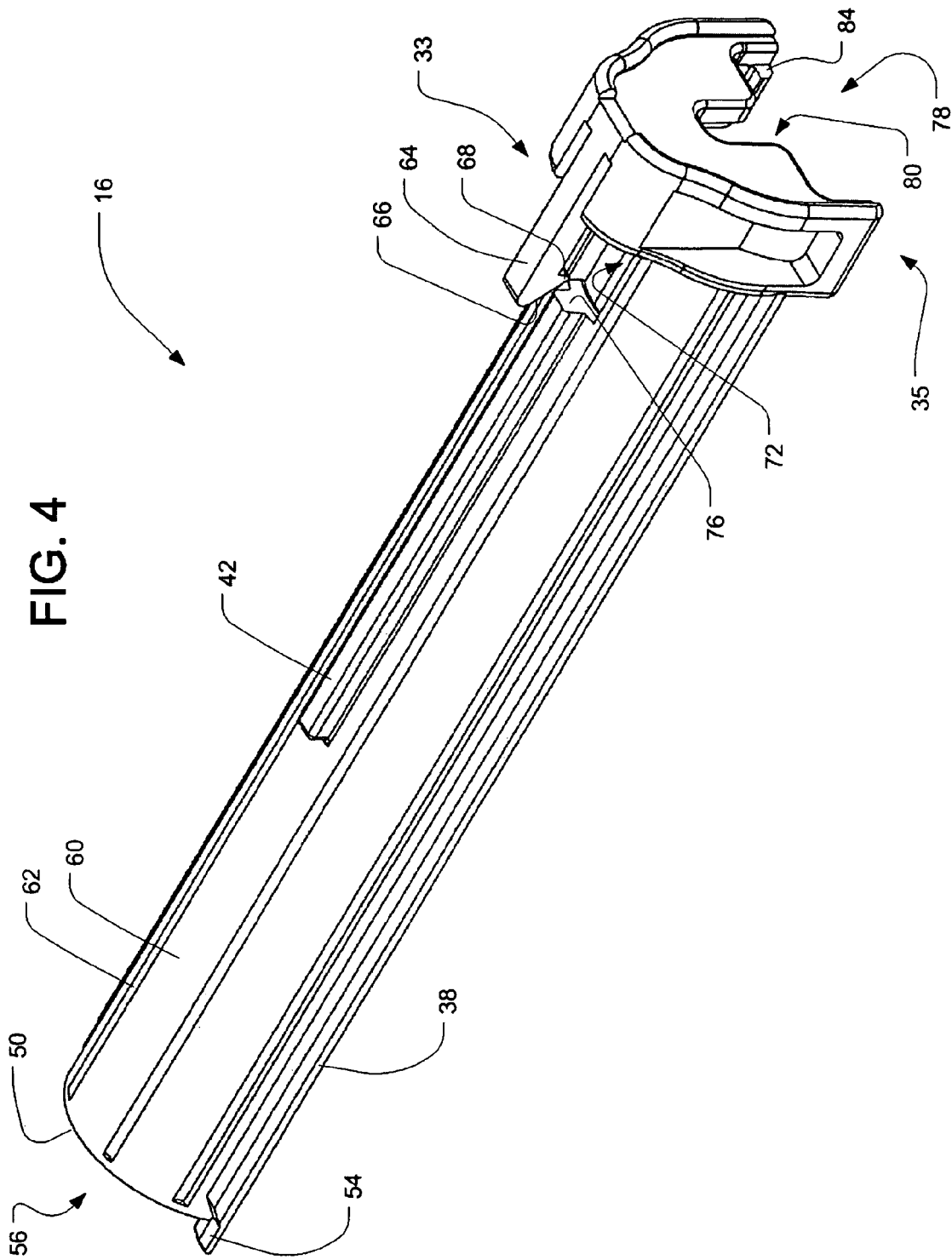
FIG. 4 is a perspective view of an aperture cover in accordance with one embodiment of the invention.

The grooves 34 formed along the inner surface 36 of the body 12 preferably extend slightly distally of the aperture 26, forming guiding recesses 52 that are configured to engage projecting members 54, which project from the distal end 56 of the aperture cover 16. The projecting members 54 are preferably aligned with and project from the distal ends of the guiding rails 38, as shown in FIG. 4. The guiding recesses 52 are preferably configured to engage the projecting members 54 as the aperture cover 16 is closing in order guide the distal edge 50 of the aperture cover 16 into proper alignment with the groove 48 in the distal edge 46 of the aperture 26.

The distal end of the passage 23 forming the open interior portion 24 preferably has a smaller diameter than the proximal end of the passage 23. For example, the cylindrical passage 23 preferably has a first generally cylindrical portion having a first diameter from the proximal end 20 of the body 12 to approximately the distal edge 46 of the aperture 26. Just distally of the distal edge 46 of the aperture 26, the inner surface 36 of the body preferably has a transition 57 having an approximately 10° slope and transitioning to a second generally cylindrical portion having a second diameter about 0.007 inches smaller than the first diameter. The change in diameter of the passage 23 distal to the aperture 26 preferably substantially prevents cement material from squeezing proximally past the rubber tip 58 of the plunger 14 when the cement is being dispensed.

FIG. 4 illustrates an aperture cover 16 in accordance with one embodiment of the present invention. The aperture cover 16 is preferably a partial, generally cylindrical shape which is configured to be received within the open interior portion 24 of the body 12. As described above, the aperture cover 16 includes guiding rails 38 along both sides of the cover 16, which are configured to engage and slide along the grooves 34 formed in the inner surface 36 of the body 12. The aperture cover 16 also includes a projection 42, which is configured to engage groove 40. As also described above, the distal edge 50 of the distal end 56 of the aperture cover 16 is configured to engage the groove 48 in the distal edge 46 of the aperture 26, and projecting members 54, which project from the distal end 56 of the aperture cover 16, engage guiding recesses 52 in order to guide the distal edge 50 of the aperture cover 16 into proper alignment with the groove 48.

Preferably the underside (not shown) of the aperture cover 16 has a partially cylindrical surface having a radius of curvature which is substantially the same as that of the cylindrical inner surface 36 of the body 12. In this way, when the aperture cover 16 is received within the body 12, the inner surface of the aperture cover 16 substantially matches the inner surface 36 of the body, forming a substantially continuous cylindrical surface.

The upper surface 60 of the aperture cover 16 preferably includes several ribs 62 projecting from the surface 60. The ribs 62 preferably contact the inner surface of the passage 23 and provide a small surface area of contact between the aperture cover 16 and the inner surface of the body 12, so that the aperture cover 16 may preferably slide relative to the body 12 with relatively little friction. The ribs 62 preferably also add structural rigidity to the aperture cover 16.

The proximal end 35 of the aperture cover 16 may include a locking member 33 which is configured to engage the projection 31 at the proximal end 20 of the syringe body 12. The locking member 33 includes a flexible snap latch arm 64 having an angled distal end 66 and a projecting tip 68. The locking member 33 operates by engaging the projection 31 with the angled distal end 66 when the aperture cover 16 is being closed. The engagement of the projection 31 with the angled distal end 66 causes the snap latch arm 64 to deflect upwards until the projecting tip 68 passes the projection 31 in the distal direction, at which point the snap latch arm 64 deflects downwards. In this position, the projecting tip 68 engages the distal end 70 of the projection 31, thus locking the aperture cover 16 in the closed position by preventing the aperture cover 16 from sliding in the proximal direction. In order to unlock the aperture cover 16, the snap latch arm 64 may simply be deflected upwards again.

The aperture cover 16 may include a feature for operatively coupling the aperture cover 16 to the plunger 14 so that both components slide together along the longitudinal axis of the syringe body 12. In that way, sliding the plunger 14 distally will cause the aperture cover 16 to close. The coupling feature may include an opening 72 in the proximal end 35 of the aperture cover 16. The opening 72 is configured to receive a portion of the coupling member 74 of the plunger 14, as will be described in more detail below. The opening 72 preferably includes an engagement portion, such as distal edge 76, for engaging a portion of the coupling member 74. The opening 72 is preferably aligned with the locking member 33 and is more preferably located under the snap latch arm 64 of the locking member 33, as shown in FIG. 4.

The aperture cover 16 is preferably aligned with the plunger 14 so that both components may slide together along the longitudinal axis of the syringe body 12. In order to maintain the alignment, the aperture cover 16 is preferably configured to engage and support a portion of the plunger 14 and to prevent rotation of the plunger 14 about the longitudinal axis of the body 12. In this regard, the aperture cover 16 includes a plunger engagement portion 78 at the proximal end 35 of the aperture cover 16. The engagement portion 78 includes a contoured portion 80 having a profile transverse to the longitudinal axis of the body 12 and configured to engage a substantially matching profile of the plunger shaft 82. In this way, the plunger 14 is preferably maintained in a fixed rotational orientation about the longitudinal axis of the body 12, and rotation of the plunger 14 with respect to aperture cover 16 is preferably prevented. This rotational constraint preferably helps keep the opening 72 in the aperture cover 16 aligned with the coupling member 74 of the plunger 14, so that the opening 72 and the coupling member 74 may readily couple together.

The engagement portion 78 preferably also includes two supporting features in the form of ledges 84. The ledges 84 are configured to engage a portion of the underside (not shown) of the contoured plunger shaft 82. By doing so, the ledges 84 preferably maintain the engagement between the plunger shaft 82 and the contoured portion 80 of the aperture cover 16. In order to secure the aperture cover 16 to the plunger 14 such that the ledges 84 engage the plunger shaft 82, the proximal end 86 of the plunger shaft 82 includes notches 88 configured to allow the ledges 84 of the aperture cover 16 to pass. Once the aperture cover 16 is coupled to the plunger 14, both components may be inserted into the passage 23 of the body 12.

Figure 5:
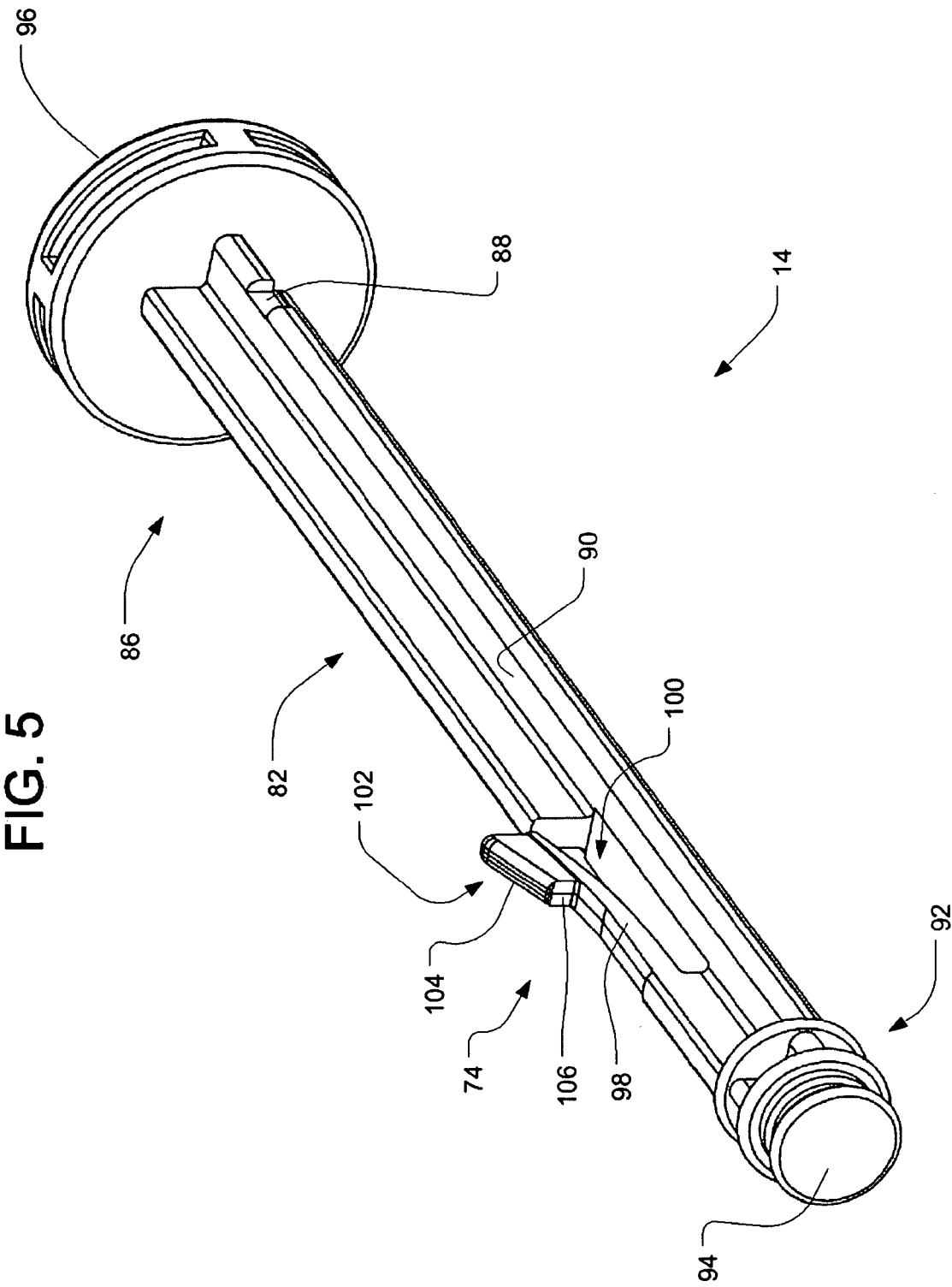
FIG. 5 is a perspective view of a plunger in accordance with one embodiment of the invention.

A plunger 14 in accordance with one embodiment of the present invention is illustrated in FIG. 5. As shown in the figure, the profile of the plunger shaft 82 in a plane transverse to the longitudinal axis of the body 12 may include four radially projecting flanges 90 forming a cross shape similar to a plus sign. The proximal end 86 of the plunger shaft 82 includes an actuator in the form of a thumb pad 96, which is configured to be depressed by the thumb of a user in order to advance the plunger 14 distally along the passage 23 of the body 12.

Figure 6:
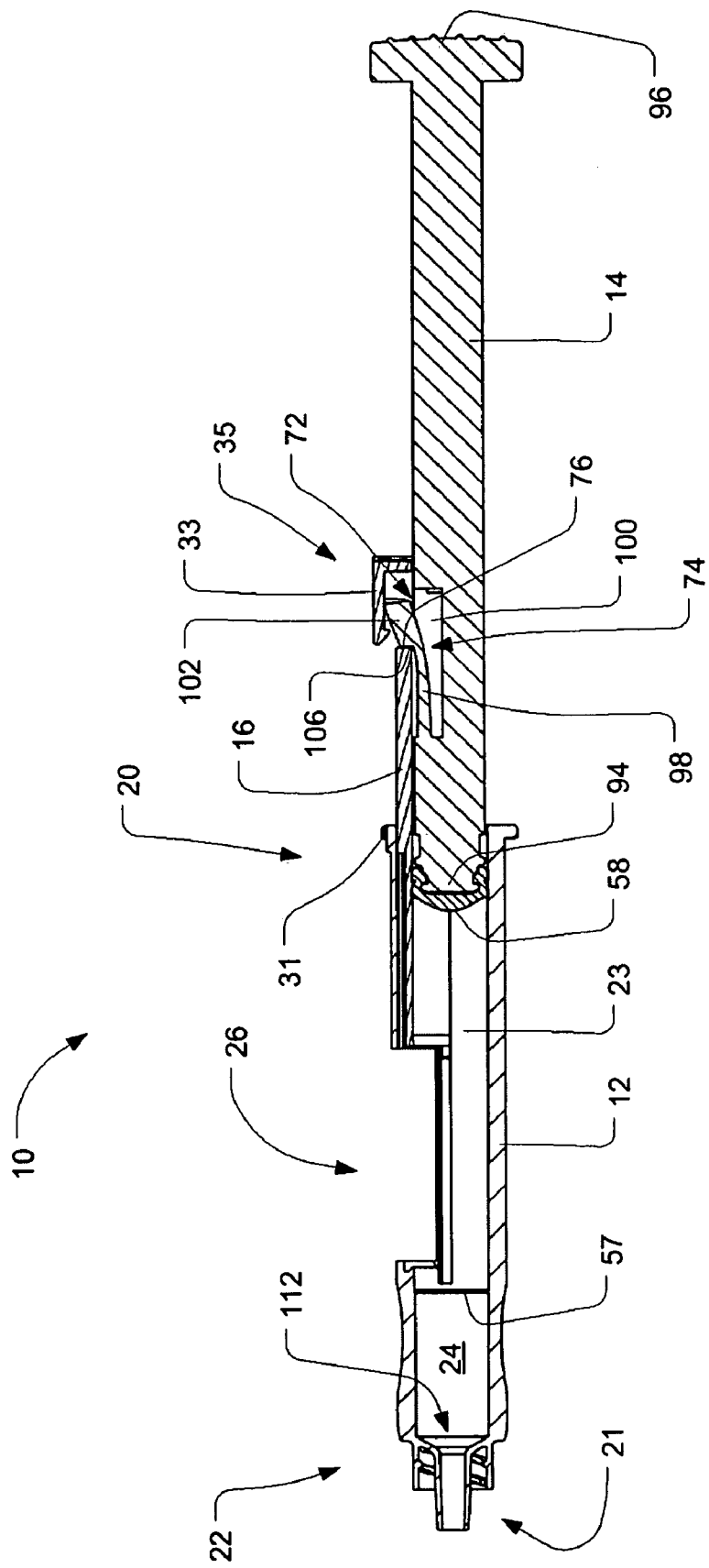
FIG. 6 is a sectional view of a syringe in accordance with one embodiment of the invention shown in a first operating state.
Figure 7:
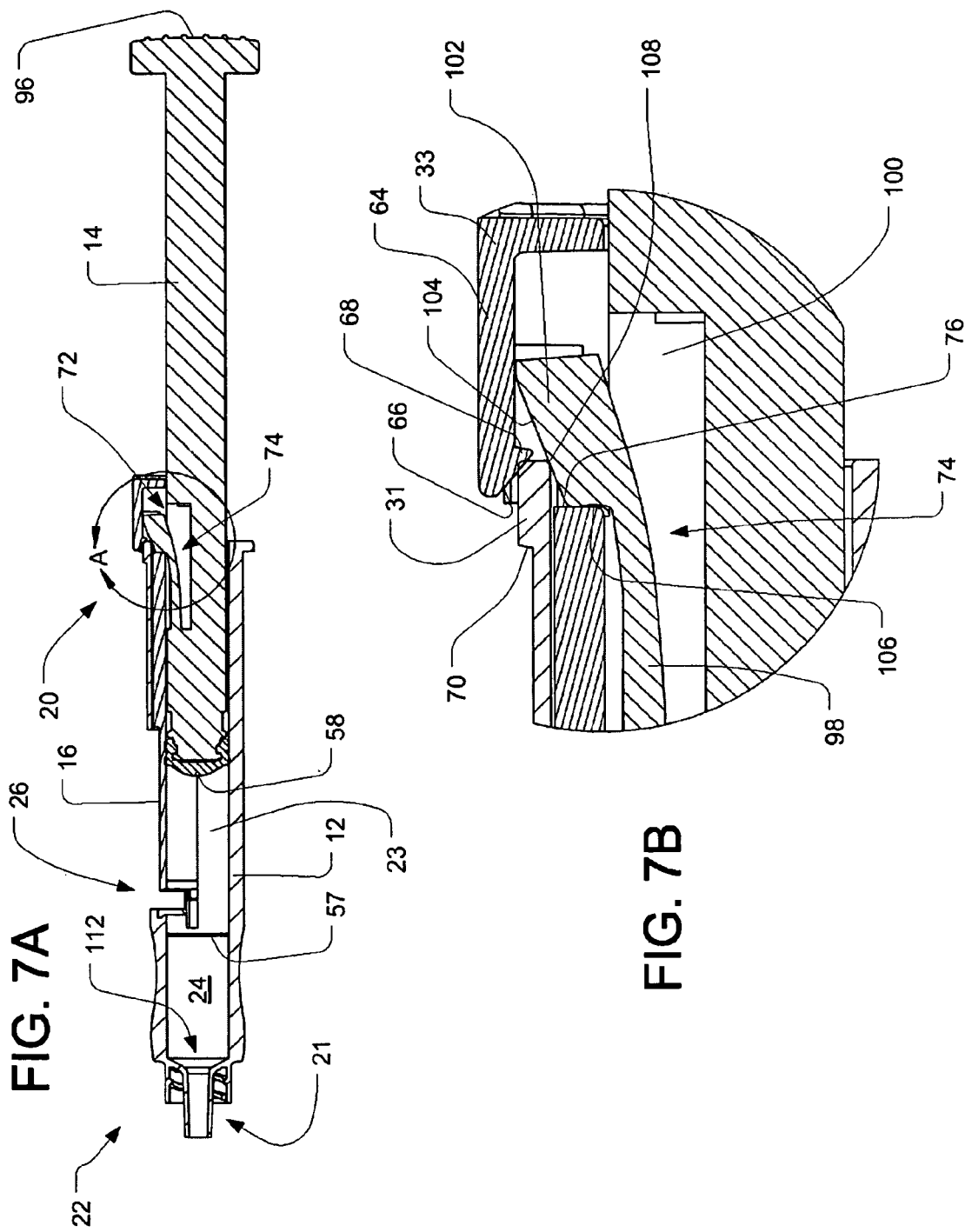
FIG. 7A is a sectional view of the syringe of FIG. 6 shown in a second operating state.
FIG. 7B is an enlarged sectional view of section A in FIG. 7A.

The distal end 92 of the plunger shaft 82 includes a tip mount 94 on which rubber tip 58 is mounted, as shown in FIG. 6. The rubber tip 58 preferably is a separate component from the plunger 14 and has a recess therein, which is mounted to the plunger 14 by inserting the tip mount 94 into the recess. The rubber tip 58 is preferably a soft elastomer which has an interference fit with the inner surface 36 of the body 12, whereby the soft material deflects as necessary during injection in order to provide a suitable seal while also maintaining relatively low frictional forces.

The coupling member 74 may be a flexible arm 98 integrally formed with the plunger shaft 82. The flexible arm 98 includes a recess 100 therebelow, in order to allow the arm 98 to flex downwards towards the longitudinal axial centerline of the plunger shaft 82. As shown in FIG. 5, the flexible arm 98 is shown integrally formed with flange 90, which flange 90 includes the recess 100 therein in order to allow the arm 98 to flex. The flexible arm 98 includes a projecting member 102 at its end. The projecting member 102 includes an angled upper surface 104 and a substantially distal facing surface 106, which surface 106 is configured to engage the distal edge 76 of the opening 72 in the aperture cover 16.

The operation of the components will now be described, with reference to FIGS. 6 through 8C. In FIG. 6, a sectional view of the components of the syringe 10 are shown in a first state, in which the aperture 26 is open and ready to be loaded with injectable material. The aperture cover 16 and the plunger 14 are both assembled to each other and to the syringe body 12 as described above. In particular, the interaction of the opening 72 in the aperture cover 16 with the coupling member 74 of the plunger 14 is shown. Specifically, the projecting member 102 of the flexible arm 98 is received within the opening 72. The distal facing surface 106 of the projecting member 102 is engaged with the distal edge 76 of the opening 72 such that, when the plunger 14 is advanced along the passage 23 towards the distal end 22, the aperture cover 16 is pushed distally due to the coupling with the plunger 14. In the first state illustrated, once the injectable material is loaded into the open interior portion 24 of the body 12 through the aperture 26, the thumb pad 96 may be depressed in order to advance the plunger 14 distally and start closing the aperture 26, by sliding the aperture cover 16 in the distal direction.

FIG. 7A illustrates a sectional view of the syringe components in a second state, in which the plunger 14 has been partially advanced along the passage 23 and the aperture cover 16 has been advanced in the distal direction such that it covers a portion of the aperture 26. In the second state illustrated, the coupling member 74 and the locking member 33 have made contact with the body 12 at the proximal end 20. As shown in FIG. 7B, which is an enlarged view of section A in FIG. 7A, the angled distal end 66 of the snap latch arm 64 of the locking member 33 is in contact with the projection 31 of the body 12. Thus, further movement of the aperture cover 16 in the distal direction will cause the arm 64 to deflect upwards, and the projecting tip 68 of the arm will ride along the top of the projection 31. FIG. 7B also shows that the angled upper surface 104 of the projecting member 102 of flexible arm 98 is in contact with a corner 108 at the proximal end 20 of the body 12. Thus, further distal movement of the plunger 14 will cause the arm 98 to flex downwards into the recess 100.

FIG. 8A illustrates a sectional view of the syringe components in a third state, in which the plunger 14 has been further advanced along the passage 23 and the aperture cover 16 has fully advanced, such that it completely covers the aperture 26, thus closing the aperture 26. As is clear from FIG. 8A, when the cover 16 is closed, the portion of the open interior portion 24 underneath the now closed aperture 26 can contain the injectable material. As shown in FIG. 8C, which is an enlarged view of section C in FIG. 8A, when the aperture 26 is closed, the distal edge 50 of the aperture cover 16 preferably securely engages the matching profile of the groove 48 of the distal edge 46 of the aperture 26 in order to prevent cement from leaking out.

FIG. 8B is an enlarged view of section B in FIG. 8A. As shown in the figure, the projecting tip 68 has passed the projection 31, and the snap latch arm 64 has deflected back downwards. The projecting tip 68 is shown engaging the distal end 70 of the projection 31, thus locking the aperture cover 16 in the closed position. That is, the interaction between the locking member 33 and the projection 31 prevents the aperture cover 16 from sliding back in the proximal direction and opening the aperture 26.

As also shown in FIG. 8B, the angled upper surface 104 of the flexible arm 98 has passed the corner 108, thus flexing the arm 98 downward such that the substantially distal facing surface 106 of the projecting member 102 is no longer engaged with the distal edge 76 of the opening 72 in the aperture cover 16. In this position, the coupling member 74 of the plunger 14 and the opening 72 in the aperture cover 16 are uncoupled, such that further distal movement of the plunger 14 will cause the angled upper surface 104 to engage a corner 110 of the distal edge 76 of the opening 72, thus flexing the arm 98 further downward into the recess 100 as the plunger 14 moves distally with respect to the aperture cover 16. Once the aperture cover 16 is uncoupled from the plunger 14, the plunger 14 is permitted to move distally along the remainder of the passage 23 while the aperture cover 16 remains locked in position. Thus, further depressing the thumb pad 96 will advance the plunger 14 further along the passage 23, where the rubber tip 58 will preferably contact the injectable material and push it towards the distal end 22 of the body 12. As is clear from FIG. 8A, the rubber tip 58 of the plunger 14 will first move through the portion of the open interior portion 24 underneath the now closed aperture 26, with the plunger sliding between the closed cover 16 and a portion of the body 12 opposite the cover, before continuing on past the cover 16 towards the distal end 22. Fully advancing the plunger along the passage 23 will preferably push the injectable material through an opening 112 at the distal end 22. The material may thus be dispensed from the distal end 22 of the body 12, or, in an embodiment where a dispensing tip 18 is attached to the distal end 22 of the body 12, the material may pass through and be dispensed from the dispensing tip 18.

The syringe of the present invention may be constructed in accordance other embodiments. For instance, the coupling member need not be included, and the aperture cover may be pushed along the longitudinal direction by contact with the plunger. For example, frictional forces resulting from the interference fit between the soft rubber tip of the plunger and the underside of the aperture cover may be sufficient to push the aperture cover into the closed position when the plunger is moved distally.

Figure 11:
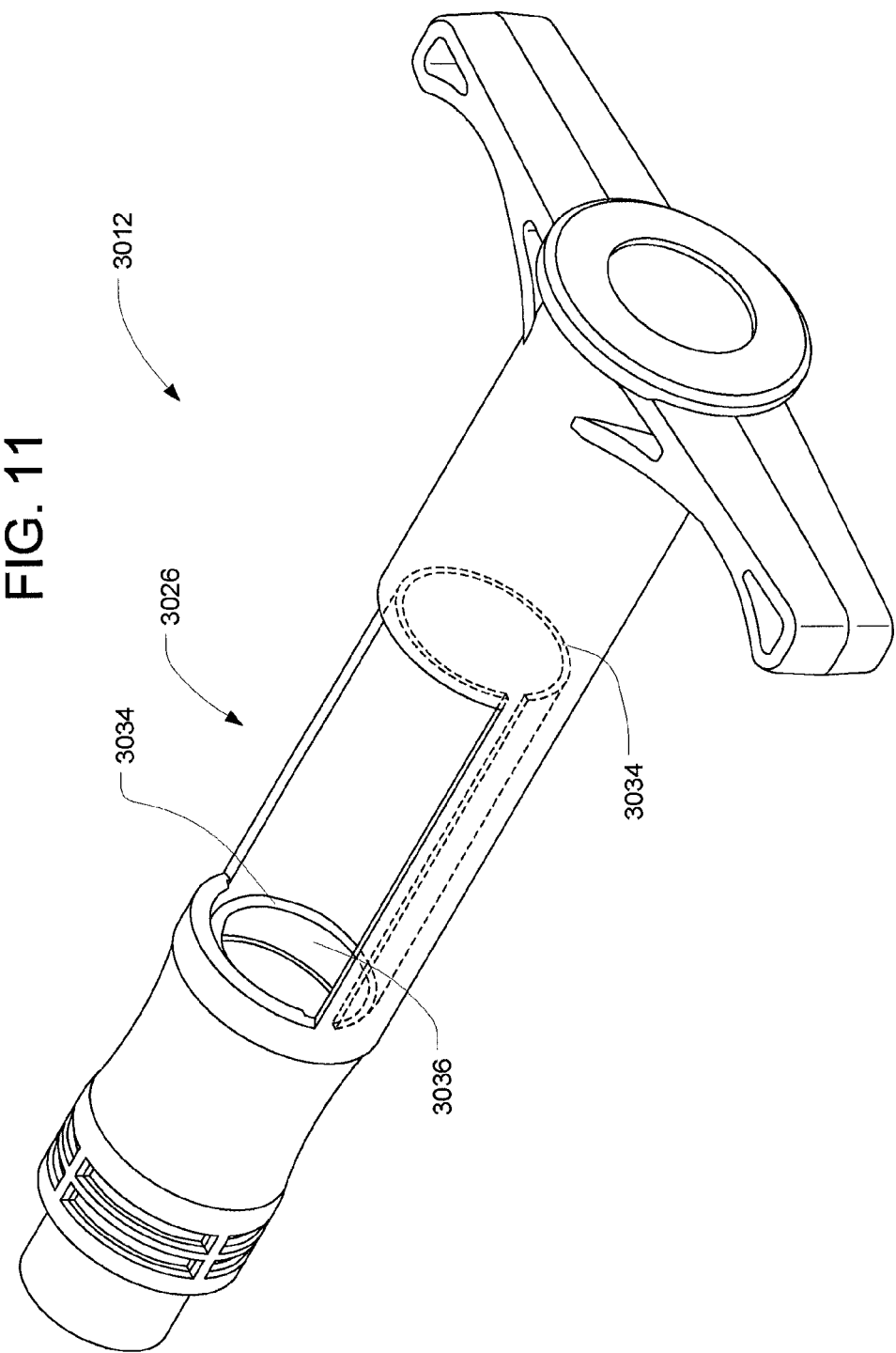
FIG. 11 is a perspective view of a syringe body in accordance with yet another embodiment of the invention.

In yet another embodiment, the aperture cover need not be linearly slid into position. For example, as shown in FIG. 11, the grooves 3034 in the inner surface 3036 of the body 3012 may follow a circular path along the circumference of the cylindrical inner surface 3036 and aligned with the aperture 3026. The coupling between the plunger and the aperture cover may thus include a mechanism for converting linear movement of the plunger into rotational movement of the aperture cover. For example, the aperture cover may include a helical feature, such as a groove, running along the cover which is configured to engage a projection on the plunger. In this way, linear movement of the plunger would cause the projection to move linearly along the passage, while the interaction with the helical groove would cause the aperture cover to rotate about the longitudinal axis of the body along the circular grooves and into a position covering the aperture.

Figure 12:
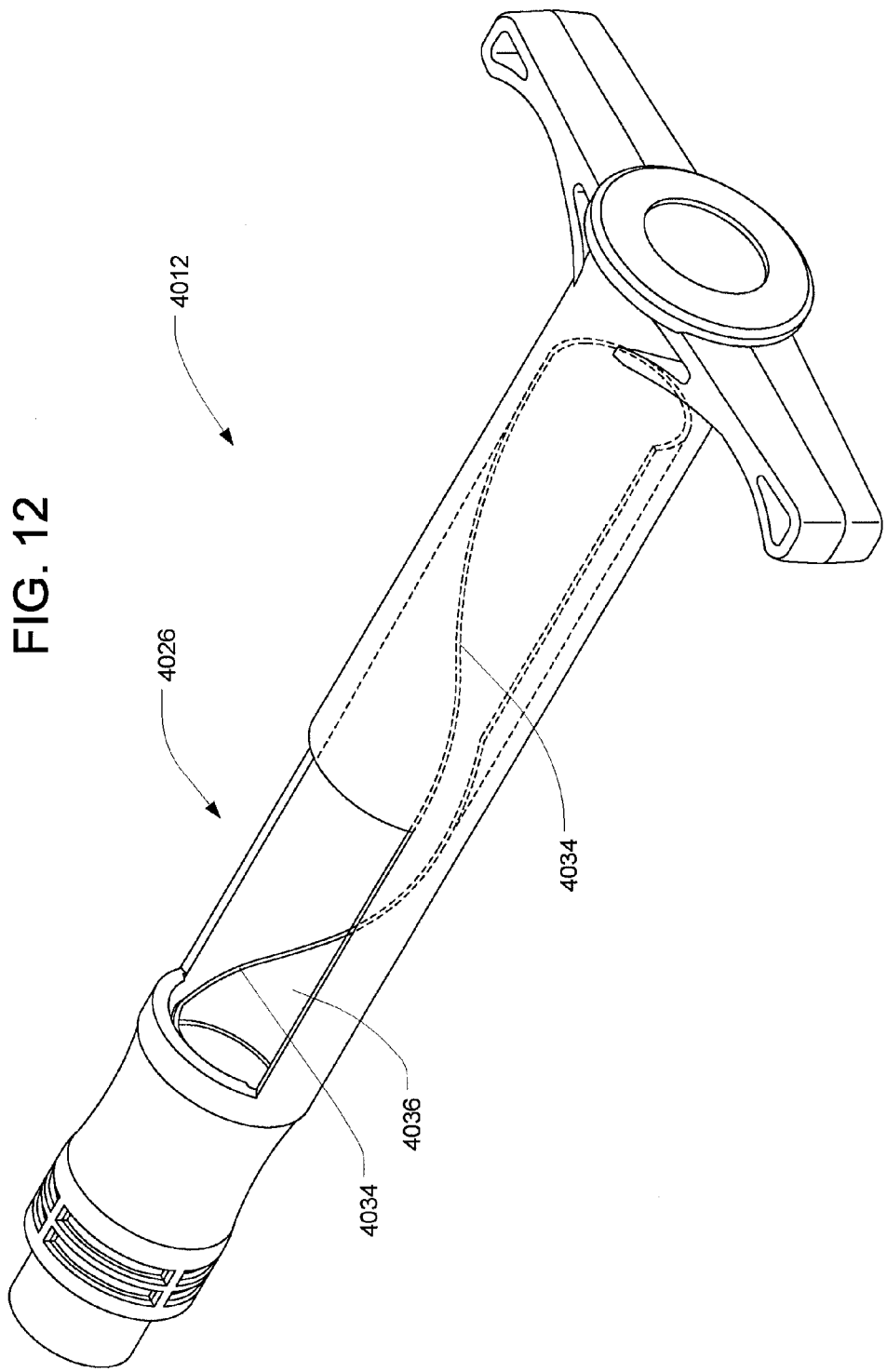
FIG. 12 is a perspective view of a syringe body in accordance with yet a further embodiment of the invention.

In yet a further embodiment, the aperture cover may follow a helical path in order to close the aperture 4026. For example, as shown in FIG. 12, the grooves 4034 in the inner surface 4036 of the body 4012 may follow a helical path along the cylindrical inner surface 4036, and the coupling between the plunger and the aperture cover may be arranged to allow the aperture cover to rotate about the longitudinal axis of the body while the plunger and aperture cover slide linearly together along the axis.

The above described embodiments of the present invention and the methods of using them preferably provide many benefits. For example, the aperture in the sidewall of the syringe preferably allows the injectable material to be easily inserted directly into the open interior portion of the syringe. Additionally, the interaction between the plunger and the aperture cover desirably simplifies the use of the syringe, as it allows one continuous stroke of the plunger to close the aperture and then dispense the material from the syringe.

The closing of the aperture cover need not be actuated by the plunger, however. Instead, in some embodiments, the aperture cover could be closed manually, independently of movement of the plunger. For example, the user could push the proximal end of the aperture cover in the distal direction, in order to close the aperture. In another example, a separate actuator connected to the aperture cover could be exposed for manipulation by the user to close the aperture cover.

In yet another alternative embodiment, the aperture cover need not be received within the body and slide into a position covering the aperture, as described above. For example, referring to FIG. 9, the body 1012 of a syringe is shown having an aperture cover 1016 hingedly attached to the body 1012. The hinge 1114 may be a living hinge integrally formed with the aperture cover 1016 and the body 1012, as shown, or it may be a separate component connecting the cover 1016 to the body 1012. The aperture cover 1016 preferably corresponds to the size and shape of the aperture 1026 formed in the body 1012, such that the aperture cover is substantially continuous with the body 1012 when the aperture 1026 is closed. The aperture cover 1016 preferably includes a locking mechanism in the form of a snap latch 1033 configured to engage a projection 1031 on the body 1012 in order to lock the aperture cover 1016 in the closed position. One benefit of this embodiment is that it effectively increases the size of the aperture 1026 because material that is placed on the underside 1116 of the aperture cover 1016 will end up in the open interior portion 1024 when the aperture cover 1016 is closed.

Figure 9:
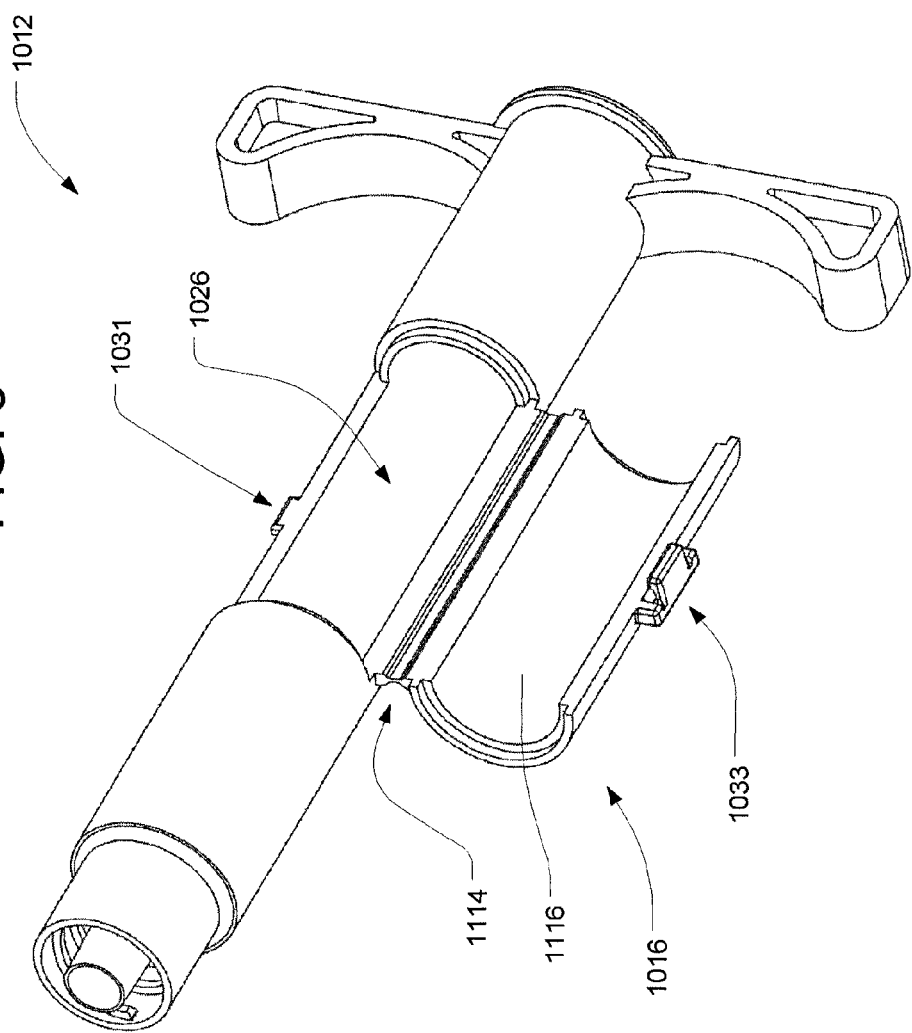
FIG. 9 is a perspective view of a syringe body in accordance with another embodiment of the invention.

In another embodiment, similar to that illustrated in FIG. 9, a hinge may not be included and the aperture cover may be an entirely separate component from the body. In such an embodiment, the syringe preferably includes a locking mechanism for securely affixing the aperture cover to the body. Such a locking mechanism may include, for example, a plurality of snap latches along the edges of the aperture cover and configured to engage corresponding projections on the body in order to secure the respective edges of the aperture cover to the body. In one example, the aperture cover may include two snap latches, where one snap latch is disposed on each edge aligned with the longitudinal axis of the body.

The syringe body of the present invention may include a standard luer connection at the distal end so that various dispensing structures can be interchangeably connected thereto. For example, dispensing tip 18, as shown in FIGS. 1-2, is a dispensing structure comprising an elongated cannulated needle 118 having an interior passage therealong through which the injectable material may flow from the opening 112 at the distal end 22 of the body 12 to an opening at the distal end 120 of the needle 118.

Figure 10:
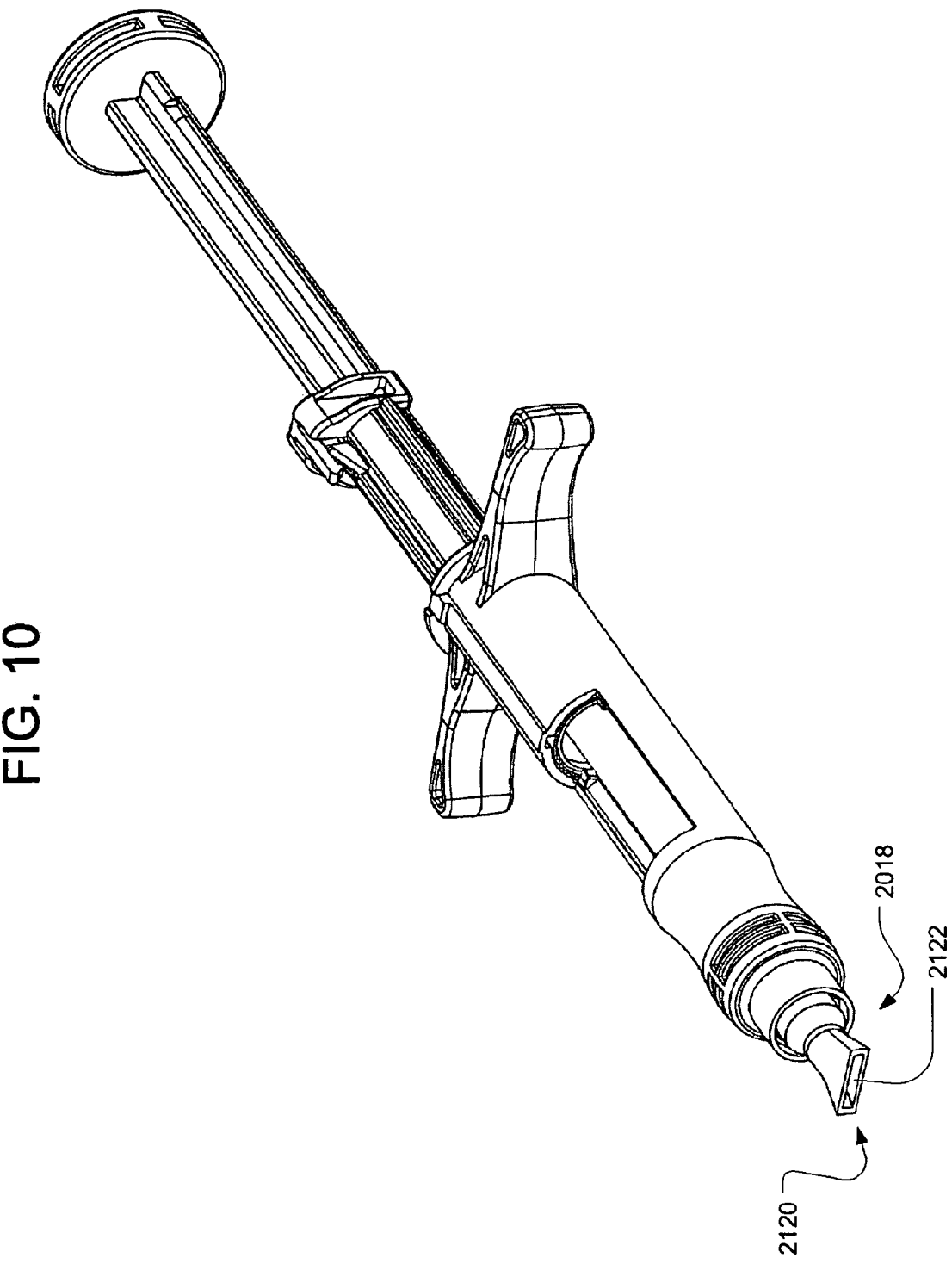
FIG. 10 is a perspective view of a syringe in accordance with another embodiment of the invention.

Another dispensing tip 2018 is illustrated in FIG. 10. Tip 2018 comprises a hollow body flaring to an opening 2122 at the distal end 2120. As shown, the opening 2122 is preferably rectangular, being wide in a first direction and narrow in a second direction perpendicular to the first direction. This design preferably allows the cement to be applied as a flat trail on the bone surface, rather than as a cylindrical bead. With a cylindrical bead, when the apposing bone portions are brought together to create a joint, the cement material generally flattens out, but may not cover the entire surface of the joint. The flared design, on the other hand, preferably allows the surface area of the bone to be more thoroughly covered during application. The distal end 2120 of the flared dispensing tip 2018 may be constructed with any of a variety of widths, depending on the application. For most bone applications in the human body, the width is preferably less than about 10 millimeters wide, and is more preferably about 5 millimeters wide. The syringe may be provided with an assortment of flared tips 2018, each having different widths for different applications.

Each of the components of each of the embodiments described above, with the exception of the rubber tip 58, are preferably composed of polycarbonate, or some similar material that offers good rigidity and biocompatibility. Rigidity may particularly be required, since the injected material may be self-curing adhesive bone cement, which may require injection forces of up to 150 Newtons.

The above-described components of the syringe in accordance with the present invention preferably come preassembled for use by the user. That is, the plunger and aperture cover are preferably connected to the syringe body in a proximal position, so that the aperture is open and ready to be loaded with injectable material. Before loading the injectable material, for example an adhesive bone cement, the material may be mixed in a mixing container shaped like a bowl. The material may then be collected by a loading device, which may have a distal end shaped like a spatula, by swiping the spatula-shaped end around the inside of the mixing container. The material may then be transferred to the open interior portion of the syringe body by inserting the distal end of the loading device into the open interior portion of the syringe body through the aperture and then retracting the loading device by swiping the distal end along an edge of the aperture so that the material is scraped off of the loading device and into the open interior portion. An illustrative example of a loading device 5002 having injectable material 5004 at the distal end 5006 thereof is shown in FIG. 3, approaching the aperture 26 of the syringe body 12. After the material is loaded into the syringe, the user may grasp the syringe in a standard manner by placing his or her fingers on the finger grips of the body and placing a thumb on the thumb pad of the plunger. The aperture may then be closed as described above and the material may be dispensed by depressing the thumb pad to advance the plunger along the passage in the body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A syringe, comprising:
an elongated body having a longitudinal axis and defining an open interior portion adapted to contain an injectable material, said body having a proximal end and a distal end, said distal end adapted to dispense the injectable material therefrom, said body including an aperture providing access to said open interior portion, said aperture being located on said body between said proximal end and said distal end;
a plunger at least partially disposed within said open interior portion of said body, said plunger configured to slide along the longitudinal axis of said body for dispensing the injectable material through said distal end; and
a closure coupled to said plunger, said closure operable to close said aperture in said body;
wherein said plunger is operable to operate said closure to close said aperture in said body, and wherein, when said aperture is closed, said plunger is slidable along the longitudinal axis of said body between said closure and a portion of said body opposite said closure.

2. The syringe of claim 1, wherein said open interior portion has a first generally cylindrical portion having a first diameter and a second generally cylindrical portion distal to said first generally cylindrical portion, said second generally cylindrical portion having a second diameter smaller than said first diameter.

3. The syringe of claim 1, wherein said plunger includes a plunger shaft having a proximal end exposed near said proximal end of said body, and an actuator attached to said proximal end of said plunger shaft.

4. The syringe of claim 1, wherein said distal end of said body has a coupling portion adapted to couple to at least one dispensing structure.

5. The syringe of claim 4, wherein said at least one dispensing structure is a cannulated needle.

6. The syringe of claim 4, wherein said at least one dispensing structure is a hollow body having a flared tip.

7. The syringe of claim 6, wherein the flared tip has a rectangular opening through which the injectable material is dispensable.

8. The syringe of claim 1, wherein said aperture has a first edge and a second edge, said first and second edges being substantially aligned with the longitudinal axis of said body, wherein an angle about the longitudinal axis defined between said first edge and said second edge has a magnitude between 90° and 180° inclusive.

9. The syringe of claim 1, further comprising a locking mechanism configured to lock said closure when said aperture is closed.

10. The syringe of claim 1, wherein said closure comprises a cover slidably coupled to said plunger, said cover configured to slide between an open position and a closed position, wherein said cover covers said aperture in the closed position.

11. The syringe of claim 10, wherein said cover is configured to slide between the open position and the closed position along a linear path, the linear path being aligned with the longitudinal axis of said body.

12. The syringe of claim 11, wherein said body includes a guiding structure configured to guide said cover along the linear path, said guiding structure preventing rotation of said cover around the longitudinal axis of said body.

13. The syringe of claim 12, wherein said plunger includes a plunger shaft oriented substantially along the longitudinal axis of said body, said plunger shaft having a first shaped profile in a plane transverse to the longitudinal axis of said body; and wherein said cover has an engagement portion configured to engage said plunger shaft, said engagement portion having a second shaped profile in the plane transverse to the longitudinal axis of said body; wherein said second shaped profile matches at least a portion of said first shaped profile, whereby said engagement portion prevents rotation of said plunger around the longitudinal axis of said body.

14. The syringe of claim 11, further comprising a locking mechanism configured to prevent movement of said cover towards the open position when said cover is in the closed position.

15. The syringe of claim 11, further comprising a coupling mechanism configured to achieve an engaged position, wherein said coupling mechanism couples said cover to said plunger when said coupling mechanism is in the engaged position, whereby said cover and said plunger slide together along the longitudinal axis of said body.

16. The syringe of claim 15, wherein said coupling mechanism is configured to achieve a disengaged position, wherein said cover is uncoupled from said plunger when said coupling mechanism is in the disengaged position, whereby said plunger is permitted to slide independently of said cover along the longitudinal axis of said body, said coupling mechanism achieving the disengaged position when said cover is in the closed position.

17. The syringe of claim 16, wherein, when said coupling mechanism is in the disengaged position, said plunger is permitted to slide towards said distal end of said body to dispense the injectable material.

18. The syringe of claim 10, wherein said cover is configured to slide between the open position and the closed position along an arcuate path, the arcuate path being aligned around the longitudinal axis of said body.

19. The syringe of claim 10, wherein said cover is configured to slide between the open position and the closed position along a helical path, the helical path being aligned around the longitudinal axis of said body.

20. The syringe of claim 10, wherein said cover has a partially cylindrical surface defining, at least in part, said open interior portion of said body.

21. The syringe of claim 10, wherein, while said cover is in the closed position, at least a portion of said plunger is movable past said cover to a location between said distal end and said aperture.

22. A syringe, comprising:
an elongated body having a longitudinal axis and defining an open interior portion adapted to contain an injectable material, said body having a proximal end and a distal end, said distal end adapted to dispense the injectable material therefrom, said body including an aperture providing access to said open interior portion, said aperture being located on said body between said proximal end and said distal end;
a dispensing means movable within said open interior portion of said body for dispensing the injectable material from said distal end of said body; and
a closing means responsive to the movement of said dispensing means for closing said aperture in said body;
wherein, when said aperture is closed, said dispensing means is movable within said open interior portion of said body between said closing means and a portion of said body opposite said closing means.

23. A method for dispensing an injectable material from a syringe, comprising:
providing a syringe having a longitudinal axis and a proximal and distal end, said syringe including an aperture therein at a location along the longitudinal axis between said proximal and distal ends, said aperture providing access to an open interior portion of said syringe and said aperture being closeable by a closure, said syringe further including a plunger moveable within said open interior portion of said syringe, said plunger being operatively coupled to said closure;
inserting an injectable material into said open interior portion of said syringe through said aperture;
depressing said plunger to sequentially close said aperture with said closure and dispense said injectable material from said distal end of said syringe, said plunger moving through at least a portion of said open interior portion of said syringe at the location of said aperture along the longitudinal axis when said aperture is closed by said closure, so as to dispense the injectable material.

24. The method of claim 23, wherein said injectable material is bone cement.

25. The method of claim 23, wherein the step of inserting said injectable material into said open interior portion comprises:
inserting a loading device having said injectable material thereon through said aperture; and
transferring said injectable material into said open interior portion.

26. A syringe for dispensing an injectable material, said syringe comprising:
a body elongated along a longitudinal axis, said body having an open interior adapted to contain an injectable material, said body having a proximal end and a distal end, said distal end adapted to dispense the injectable material therefrom, said body having a lateral aperture providing access to the open interior of said body, said aperture being located on said body at a location along the longitudinal axis between said proximal end and said distal end;
a plunger slidably received at least partially within said open interior of said body, said plunger moveable between at least a first and second position within said body; and
a cover operatively coupled to said plunger, such that movement of said plunger to the second position operates said cover to close said aperture;
wherein, when said aperture is closed by said cover, said plunger is adapted to move through at least a portion of said open interior of said body at the location of said aperture along the longitudinal axis, so as to dispense the injectable material through said distal end.

27. The syringe of claim 26, wherein said cover is configured to slide along a linear path, the linear path being aligned with a longitudinal axis of said body.

28. The syringe of claim 27, wherein said body includes a guiding structure configured to guide said cover along the linear path, said guiding structure preventing rotation of said cover around the longitudinal axis of said body.

29. The syringe of claim 26, further comprising a locking mechanism configured to prevent said aperture from opening when said aperture is closed by said cover.

30. The syringe of claim 26, wherein said cover becomes uncoupled from said plunger when said aperture is closed, whereby said plunger is permitted to move independently of said cover within said body.

31. The syringe of claim 30, wherein said body has a dispensing end adapted to dispense the injectable material therefrom, and wherein, when said aperture is closed by said cover and said cover is uncoupled from said plunger, said plunger is permitted to slide towards said dispensing end of said body to dispense the injectable material.

32. The syringe of claim 26, wherein said plunger is moveable to a third position beyond the first and second positions, the injectable material having been dispensed from said body when said plunger is in the third position.

33. The syringe of claim 26, wherein said cover has a partially cylindrical surface defining, at least in part, said open interior of said body.

34. The syringe of claim 26, wherein said body has a dispensing end adapted to dispense the injectable material therefrom, and wherein, when said aperture is closed by said cover, at least a portion of said plunger is movable past said cover to a location between said dispensing end and said aperture.

35. A syringe, comprising:
an elongated body having a longitudinal axis and defining an open interior portion adapted to contain an injectable material, said body having a proximal end and a distal end, said distal end adapted to dispense the injectable material therefrom, said body including an aperture providing access to said open interior portion, said aperture being located on said body at a location along the longitudinal axis between said proximal end and said distal end;
a plunger at least partially disposed within said open interior portion of said body, said plunger configured to slide along the longitudinal axis of said body for dispensing the injectable material through said distal end; and
a cover slidably coupled to said plunger, said cover configured to slide between an open position and a closed position, wherein said cover covers said aperture in the closed position;
wherein said plunger is operable to slide said cover to the closed position, wherein said cover is structured such that at least a portion of said open interior portion of said body at the location of said aperture along the longitudinal axis can contain the injectable material when said cover is in the closed position, and wherein, while said cover is in the closed position, at least a portion of said plunger is movable past said cover to a location between said distal end and said aperture.

36. The syringe of claim 35, wherein said cover becomes uncoupled from said plunger when said cover is in the closed position, whereby said plunger is permitted to slide independently of said cover along the longitudinal axis.

* * * * *